(12) United States Patent
King

(10) Patent No.: US 8,591,735 B2
(45) Date of Patent: Nov. 26, 2013

(54) DRINKING WATER PURIFICATION DEVICE

(76) Inventor: Joseph A. King, Wayzata, MN (US)

( * ) Notice: Subject to any disclaimer, the term of this patent is extended or adjusted under 35 U.S.C. 154(b) by 583 days.

(21) Appl. No.: 12/803,966

(22) Filed: Jul. 9, 2010

(65) Prior Publication Data

US 2010/0307976 A1  Dec. 9, 2010

Related U.S. Application Data

(60) Continuation-in-part of application No. 12/315,285, filed on Dec. 2, 2008, now Pat. No. 7,875,191, which is a continuation of application No. 11/999,654, filed on Dec. 6, 2007, now Pat. No. 7,501,067, which is a division of application No. 10/928,668, filed on Aug. 26, 2004, now Pat. No. 7,347,934, application No. 12/803,966, which is a continuation-in-part of application No. 12/386,074, filed on Apr. 14, 2009, which is a continuation-in-part of application No. 12/001,351, filed on Dec. 11, 2007, now Pat. No. 7,556,515.

(51) Int. Cl.
*C02F 1/68* (2006.01)
*B01D 15/04* (2006.01)

(52) U.S. Cl.
USPC ............ 210/206; 210/209; 210/241; 210/282

(58) Field of Classification Search
USPC ......... 210/663, 749, 753, 754, 755, 764, 205, 210/206, 209, 241, 282, 287–289
See application file for complete search history.

(56) References Cited

U.S. PATENT DOCUMENTS

| | | | | |
|---|---|---|---|---|
| 3,327,859 A | * | 6/1967 | Pall ............................... | 210/282 |
| 4,198,296 A | * | 4/1980 | Doumas et al. ............... | 210/668 |
| 2008/0156739 A1 | * | 7/2008 | King ............................. | 210/205 |

* cited by examiner

*Primary Examiner* — Lucas Stelling
(74) *Attorney, Agent, or Firm* — Jacobson & Johnson LLC

(57) ABSTRACT

A fast acting water purification system containing a source of silver ions which is suitable for use in personal or household water containers, where the non-potable water may contain halides or other materials that limit the solubility of silver in the non-potable water, with the purification agent including a source of silver ions and a compound containing a hydantoin ring increase the presence of silver ions in the non-potable water to a level sufficient to quickly kill harmful microorganisms in the non-potable water without the need to add additional biocides to the non-potable water or pretreat the non-potable water.

6 Claims, 4 Drawing Sheets

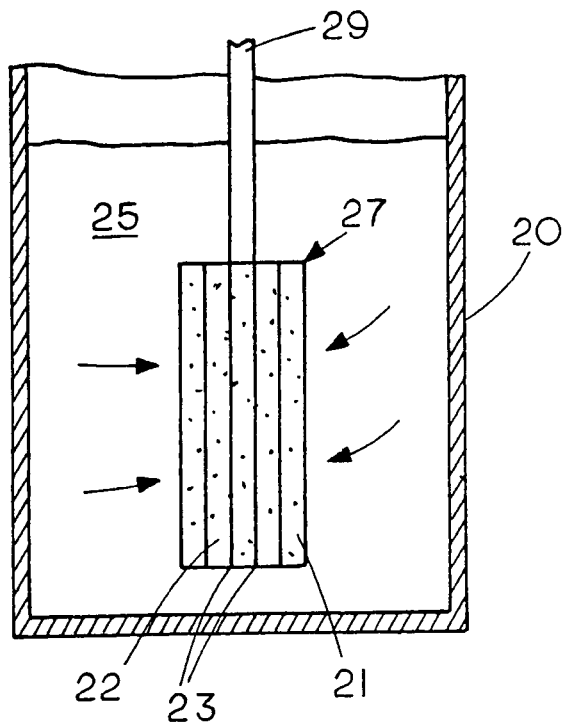
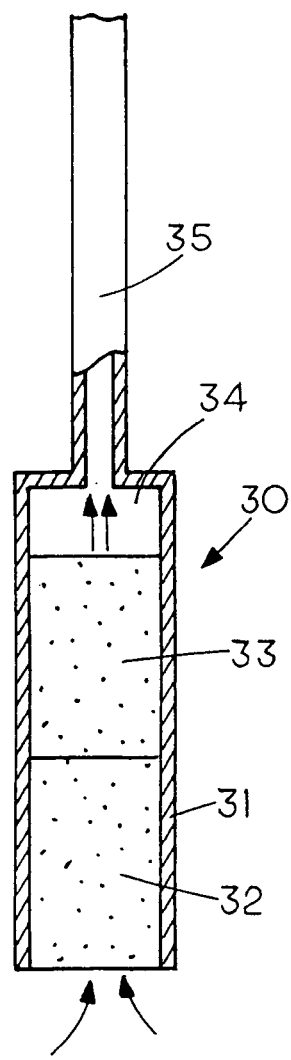
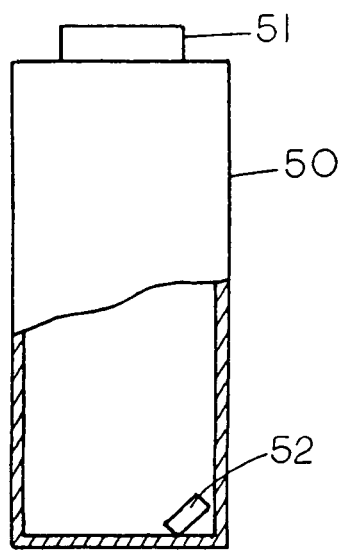

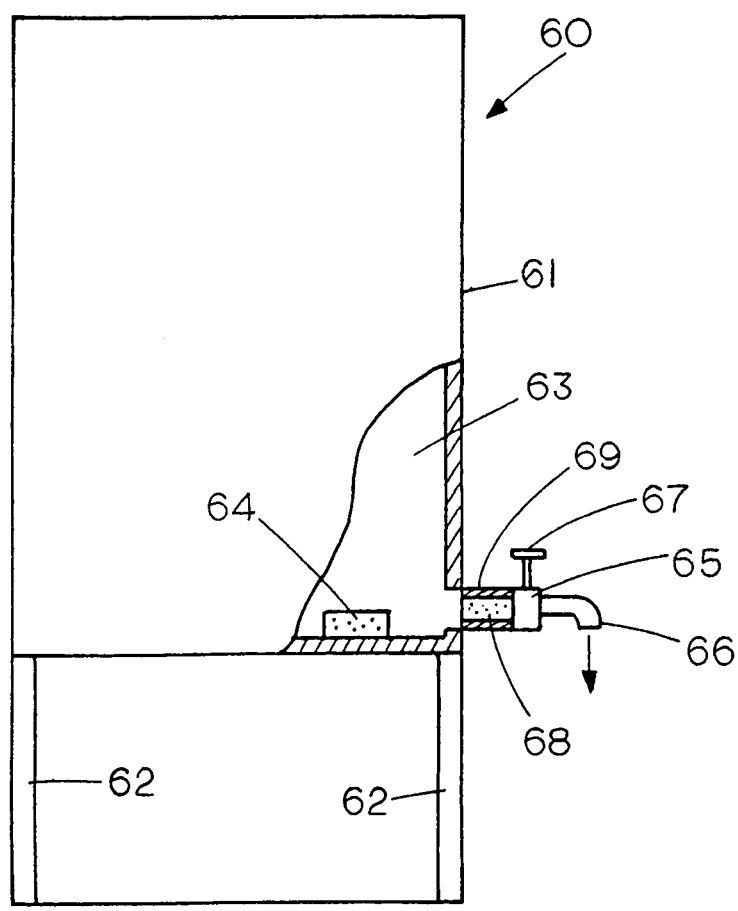

DRINKING WATER PURIFICATION DEVICE

CROSS REFERENCE TO RELATED APPLICATIONS

This application is a continuation-in-part of U.S. application Ser. No. 12/315,285 filed Dec. 2, 2008 now U.S. Pat. No. 7,875,191 which is a continuation of application Ser. No. 11/999,654 filed on Dec. 6, 2007 now U.S. Pat. No. 7,501,067, which is a division of application Ser. No. 10/928,668 filed on Aug. 26, 2004, which is now U.S. Pat. No. 7,347,934; and U.S. application Ser. No. 12/386,074 filed Apr. 14, 2009 which is a continuation in part of U.S. application Ser. No. 12/001,351 filed Dec. 11, 2007 now U.S. Pat. No. 7,556,515.

FIELD OF THE INVENTION

This invention relates generally to water purification and, more specifically, to purifying small amounts of non-potable water in portable containers or in household containers where the non-potable water may contain compounds that inhibit the effectiveness of the water purification material.

STATEMENT REGARDING FEDERALLY SPONSORED RESEARCH OR DEVELOPMENT

None

REFERENCE TO A MICROFICHE APPENDIX

None

BACKGROUND OF THE INVENTION

The purification of small amounts of non-potable water for individuals or households has been accomplished through various methods. Some methods involve pumping water through a filter to remove harmful bacteria while still other methods use chemicals such as halogens including chlorine, bromine and iodine. Some methods, which use a source of silver ions as a disinfectant, require one to pretreat the water in order to use silver ions purify the water.

One of the difficulties in creating potable water in small amounts is the need to quickly generate potable water from non-potable water. U.S. Pat. No. 6,010,626 shows a pump that quickly generates potable water by forcing nonpotable water through a filter to remove bacteria and other debris. While such devices can work effectively for filtering out certain types of bacteria they usually require extensive hand pumping to generate a small amount of potable water since a large force is required to force the water through the small pores in the filter. A variety of different methods and apparatus are used to render non-potable water potable as evidenced by the following patents:

U.S. Pat. No. 4,894,154 shows an example of an individual portable water treatment device that uses a pleated membrane-filtering cartridge.

U.S. Pat. No. 7,390,343 shows a device for removing harmful organisms from non-potable water with nano alumina fibers having particles of metals such as silver, copper or zinc deposited on the nano alumina fibers.

U.S. Pat. No. 4,349,512 shows an improved bacteriostatic filter media for home use that uses a bacteriostatic filter media comprising silver treated cellulose and powdered carbon.

U.S. Pat. No. 4,267,455 shows another type of a water purification device that uses UV tubes that extend through a chamber in the vessel.

U.S. Pat. No. 7,441,665 discloses a water purification cartridge for use in a gravity feed filtration discloses the use of a water purification medium that may include a halogenated polystyrene hydantoin, a halogenated polymeric sulfonamide resins, a halogenated hydantoin siloxane and a halogenated polystyrene traiznedione.

U.S. Pat. No. 4,695,379 discloses a water treatment bottle that includes a cap that can be placed on a bottle with the cap including a tube that contains a water treatment material such as carbon, silver impregnated coral sand, ion exchange resins to remove contaminants normally present in tap water.

U.S. Pat. No. 4,198,296 shows pretreating the water to remove halide ions so that the silver ions from the silver activated charcoal media can disinfect the water.

Some of the difficulties with the aforedescribed devices and methods is that some types of filtration device require considerable work on part of the user to generate potable water thus discouraging their use. Still others require an extended length of time for the purification agent to render the water potable and still others require pretreatment of the water before the water can be disinfected.

SUMMARY OF THE INVENTION

A fast acting water purification system containing a source of silver ions which is suitable for use in personal or household water containers, where the non-potable water may contain halides or other materials that limit the solubility of silver in the non-potable water, with the purification agent including a source of silver ions and a compound containing a hydantoin ring whereby the compound containing a hydantoin ring is added to increase the solubility of silver ions in a body of water above the natural solubility of silver ions in the non-potable water to thereby increase the presence of silver ions in the non-potable water to a level sufficient to quickly kill harmful microorganisms in the non-potable water without the need to add additional biocides to the non-potable water or pretreat the non-potable water.

BRIEF DESCRIPTION OF THE DRAWINGS

FIG. 4 shows a water purification member for placement in a container to obtain potable water;

FIG. 5 shows an alternate embodiment of water purification for on-the-go generating of small amounts of potable water;

FIG. 6 shows a container containing a tablet containing silver and a hydantoin for generating a container of potable water;

FIG. 7 shows a household container including a water purification material for generating sufficient potable water for a small household;

DESCRIPTION OF THE PREFERRED EMBODIMENT

While a source of silver ions has been widely used as a water-purifying agent in various water purifying applications the limitation of the natural solubility of silver in the non-potable water can adversely affect the ability of the silver to quickly kill harmful organisms in the non-potable water. For example, because of the limited solubility of silver in water one may require an extended contact time of the silver ions before the harmful microorganisms in the water are killed. In some cases the natural solubility of silver in the nonpotable water may be insufficient to purify the water since the rate of microorganisms growth may exceed the potential kill rate of the silver based water purification agent. In these cases other biocidal agents have been used in conjunction with silver to kill harmful organisms and in still other cases halides or halogens that may interact with the silver ions must be removed from the non-potable water before the silver ion based purification agent can be used to disinfect the water.

Figure 1:
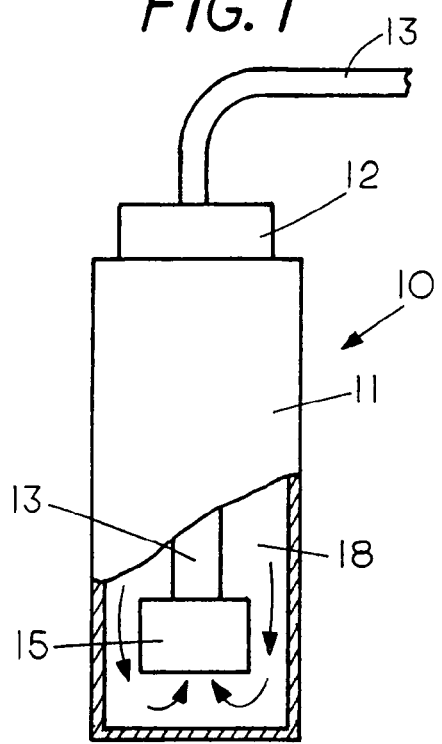
FIG. 1 is a partial sectional view of a hand held water purification device.

FIG. 1 shows an example of a hand held water purifier 10 comprising a container 11 having a cover or cap 12 with a drinking tube 13 extending through the cap 12 and into a chamber 18. Located in chamber 18 is the water purification material, which is contained within housing 15. Container 11 may be a typical polymer plastic water bottle with a screw top cap that is sufficiently small to allow one to carry the bottle as a person goes about their daily activities. Usually, such containers contain a quart or less of water which enables them to be easily carried from place to place. The screw top cap on the container permits one to obtain quick access to chamber 18 to allow one to periodical refill the container with non-potable water once the potable water in the container has been consumed. A feature of the drinking tube 13 is that it allows one to draw potable water on demand from the chamber 18. In this example of the invention the non-potable water in the container 11 can be quickly purified i.e. on the go by the water purification material located in housing 15 even as water is being drawn through drinking tube 13.

Figure 2:
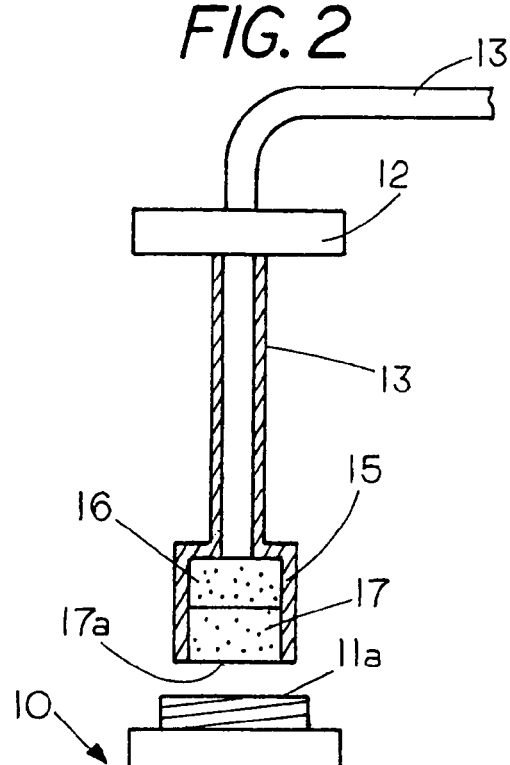
FIG. 2 is an exploded view of the hand held water purification device of FIG. 1.

FIG. 2 shows the hand held water purifier 10 of FIG. 1 in an exploded view with a lower portion of a drinking tube 13 and housing 15 in section view. As can be seen the water purification material 17, which includes a source of silver ions, is retained in the in the lower end of housing 15 with the water purification material 17 having an exposed face 17a for contact with nonpotable water placed in container 11. The water purification material 17 may be supported on an inert porous carrier to permit water to flow threrethrough. Positioned downstream and in series with the water purification material 17 is a filter media 16 which for example may include carbon particles or an ion exchange resin. In operation of the hand held water purification device 10 a person can grasp container 11 in one hand and suck on tube 13 to draw water from container 11 through the water purification material 17, filter 16 and tube 13. In the example shown the water purification material 17 includes a source of silver ions such as silver chloride, which is supported on a carrier. The carrier may be either a solid or porous structure that is suitable for securing the silver chloride thereto, typically by an adhesive or the like which allows the silver ions to be released into the nonpotable water. In addition to the source of silver ions in the water purification material 17 the water purification material includes a compound containing a hydantoin ring where the compound containing the hydantoin ring may or may not have any biocidal properties. As an option a filter media 16 of a selected pore size may be located downstream of the water purification material to remove organic particles or other types of larger particles that may be present in the non-potable water. Although silver chloride is described as a source of silver ions other sources of silver ions may be used including silver metals without departing from the spirit and scope of the invention described herein.

In the conventional process of purifying water it is known the availability of silver ions for killing harmful microorganisms is limited by the natural solubility of the silver ions in water. That is, during the water purification phase the silver ions, which are gradually consumed in the water purification process, are replaced by fresh silver ions which are available from a source of silver ions in the water. Replacing the spent silver ions with fresh silver ions allows one to maintain the level of available silver ions at the natural silver ion solubility level. In general, the lower the solubility of silver in water the longer the time needed for the silver ions to kill harmful organisms in the water since at any moment there are limited amounts of silver ions available to kill harmful organisms. Thus a limiting factor in water purification using silver ions may be the time required to purify the water in the container because of the limited availability of fresh silver ions to replace the spent silver ions. In other cases the natural solubility of silver ions in the non-potable water may be insufficient to purify the water since the level of silver ions may be inadequate to overcome the growth of microorganisms. The addition of a compound containing a hydantoin ring, such as dimethylhydantoin (DMH), increases the solubility of silver in water and hence the quantity of silver ions present in the water even though the compound of itself may have no biocidal properties. That is the compound containing a hydantoin ring when used alone lacks the ability to purify water.

Increasing the level of silver ions in the water reduces the time to bring the water to a purified stated since more silver ions are immediately available for killing unwanted microorganisms. For example, with the invention described herein one can maintain the level of silver ions in water at levels 2 to 3 times greater than is normally found where silver ions are used as the sole water purification agent by adding DMH to the water to increase the solubility of silver ions in the water and hence the ability to rid the water of harmful microorganisms. Thus, the addition of DMH to the water allows one to maintain a higher level of silver ions in the water, which permits the consumed silver ions to be quickly replaced with fresh silver ions from the source of silver ions in the non-potable water which in turn reduces the time to bring the non-potable water to a potable state. The level of solubility of silver in non-potable water may be limited by a number of factors including the presence of halides in the non-potable water. In addition the presence of other materials limit the solubility of silver in the non-potable water. With the invention described herein one can increase the level of silver ions in the non-potable water to levels that are such that the source of silver ions is the sole means for quickly and effectively rendering non-potable water potable.

To avoid the possibility of skin discoloration due to argosies the EPA has adopted 50 ppb or less of silver as an acceptable level of silver for potable drinking water, however, in some countries the levels of silver are not limited since the adverse effects of consuming non potable water are considerably greater than the cosmetic effects of skin discoloration due to argosies. In the event one wants to lower the level of silver ions in the water after the water has been purified but before the water is ingested the purified water can be directed through a filter media such as an ion exchange medium to remove silver ions or bring the level of silver ions down to levels of 50 ppb or less.

In the invention described herein one can limit the concentration or solubility of silver by controlling the concentration of DMH in the water. For most applications a concentration of 5 ppm DMH is sufficient to increases the solubility of silver to levels that will quickly and effectively kill bacteria, however, the concentration of DMH and the availability of silver may be selected depending on the end use. For example one may add sufficient DMH to maintain the solubility of silver less than 50 ppb which maintains the concentration of silver below current EPA guidelines or one may add sufficient DMH to maintain the silver ion concentration in excess of 50 ppb.

The use of silver chloride together with a compound containing a hydantoin ring creates a water purification material 17 that increases the solubility of silver ions in water and hence the ability of the silver ions to kill harmful organisms without the addition of additional water purification agents even though the compound containing the hydantoin ring may lack any biocidal properties. A suitable compound containing a hydantoin ring for enhancing the solubility of the silver is Dimethylhydantoin (DMH) although other compounds contain a hydantoin ring may be used. An advantage in use of DMH is that DMH is not known to contain any complexes that may be harmful if consumed. Another suitable hydantoin which lacks harmful complexes is glycolylurea.

In the example of FIG. 2 the housing includes an optional filter media 16 which may be carbon. Carbon filters are generally used to improve the taste of water by removing unwanted materials from the water. The carbon filter may comprise particles or granules of carbon selected by size so as to block passage of particles exceeding a certain dimension. Other examples of filter media 16 that may be used include ion exchange resins. An advantage of an ion exchange resin is it provides a convenient way to prevent the flow of silver ions into the drinking tube 13 since the silver ions can be trapped by the ion exchange resin in filter 16. Thus in one example of the invention a filter media 16 may be used to limit the level of silver ions in the potable water which is being ingested through drinking tube 13.

An advantage of the described use of a water purification material utilizing DMH is that it that the level of silver ions in the container containing non-potable water can be elevated to levels sufficient to quickly and effectively kill harmful organisms and thus eliminate the need for supplemental water purification agents or the need to pretreat the non-potable water. Thus, through control of the level of silver ions in the water by the addition of DMH one can enhance the solubility of silver to thereby increase the effectiveness of the water purification material. Since the water purification material with a source of silver ions and the compound containing a hydantoin ring such as DMH can effectively kill harmful organisms in the water the use of filter media 16 to remove silver ions becomes option which may be dependent on the needs, likes or dislikes of the user.

While it is understood that in some cases the normal silver solubility in the non-potable water may be sufficient to maintain low bacterial levels if sufficient contact time is available. In other cases one may want to maintain a higher level of silver ions to more quickly and effectively bring the non-potable water in the container to a potable state by increasing the solubility of silver in the non-potable water. For example, with one type of non-potable water maintaining a level of silver ions at 10-15 ppb may quickly and effectively kill bacteria and other harmful organism including viruses. In other types of non-potable water having higher bacteria levels one may have to increase the level of silver ions in the potable water to levels in excess 100 ppb in order to obtain a quick kill of harmful organisms. In both cases one can elevate the level of silver ions in the body of water and hence the biocidal effectiveness of the water purification material by increasing the solubility of silver in the body of water through the addition of a compound containing a hydantoin ring even though the compound containing the hydantoin ring may or may not have any biocidal properties. In general increasing the level of the compound containing a hydantoin ring increases the solubility of silver in the body of water. Thus a user has the option of selecting and controlling the level of silver ions in the non-potable water by controlling the amount of the compound containing a hydantoin ring in the presence of non-potable water. This feature enables the water purification materials to be used on a variety of different types of non-potable water, some which may require extensive purification and others which may require minimal purification.

Figure 3:
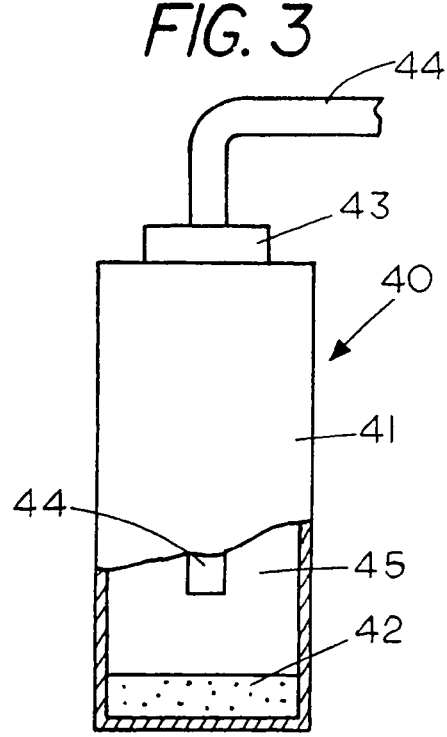
FIG. 3 is another embodiment of a hand held water purification device.

FIG. 3 shows an example of another embodiment of a hand held water purifier 40 that includes a container 41, which is suitable for holding in a user's hand. The water purification material 42 is located on the bottom of the container and typically comprises a source of silver ions such as silver chloride with a hydantoin such as DMH to generate levels of silver ions sufficient to maintain the water in the container 41 free of bacteria and other harmful organisms. To use the hand held water device 40 the user draws water into his or her mouth through the tube 44 that extends into the chamber 45 which contains the water which is being rid of harmful organisms by the purification agent in the water purification material 42. In this application an additional filter is not used and the water purification agent in the water purification material 42 is affixed to the inside of the container to allow for repeated refilling of the water container.

FIG. 4 shows a cross sectional view of another example of a water purification device. Reference numeral 20 identifies a lower portion of a container which contains a water purification device 27 that's includes a drinking tube 29 that is connected to a pleated filter 23 for removing organic matter. Filter 23 also includes a source of silver ions such as silver chloride 21 as well as a compound 22 containing a hydantoin ring. The source of silver ions and the compound containing the hydantoin ring are dispersed over the surface of the filter 23. In this example the user draws drinking water through tube 25 with the pleated filter 23 removing unwanted particles of material from the drinking water at the same time the water is being purified by the presence of silver ions.

FIG. 5 shows an example of another water purification device or container 30 that can be placed in an open source of water with the water being purified as it is drawn through filter media 32. Filter media 32 includes a source of silver ions and a compound containing a hydantoin ring. In this example the filter media 32 is located in the lower end of an outlet housing 31 to enable the water purification material to come into direct contact with the non-potable water before it is drawn into drinking tube 35, which extends from the upper end of housing 31. The upper end of housing 31 may include a filter media, for example, a carbon filter 33 to improve the taste of the water by removing organic material from the water. In operation of water purification device 30 water is drawn through filter media 32 carbon filter 33 and into plenum chamber 34 where it is drawn through tube 35 to be ingested by the user. This type of water purification device permits a user to insert the water purification device directly into another water container or an open source of water such as a lake or stream to thereby quickly kill the harmful organisms before they can be ingested. While the device shown in FIG. 5 is used with a carbon filter 33 the device may be used without the carbon filter 33 at the user's option.

Thus FIG. 5 discloses a method of purifying water immediately prior to consumption of the water by introducing a non-potable water, where the non-potable water may contain halides, into a housing 31 and bringing the non-potable water into contact with a source of silver ions and a compound containing a hydantoin ring which is retained in porous filter media 32 by sucking on drinking tube 35. The filter media 32 increases the natural water solubility of silver ions in the non-potable water to thereby quickly convert the non-potable water into potable water by exposing the non-potable water to the source of silver ions and the compound containing a hydantoin ring which are retained in filter media 32. The water purification occurring prior to consuming the potable water by drawing the water through the filter media 33 and into chamber 34 where it can be made available for consumption.

FIG. 6 shows another example of a hand held water purifier comprising a container 50 having a removable cover 51 with a pellet or tablet 52 therein that in one example contains a source of silver ions and a compound containing a hydantion ring. A suitable material for the pellet or tablet may be silver chloride and a suitable compound containing a hydantoin ring may be DMH. In this example the pellet may contains just enough water purification materials to purifier a single container of non-potable water or if desired the pellet may be sufficiently large so that the container 50 can be refilled multiple times. In some cases the pellet or tablet may be dissolvable in water. While a large number of compounds containing a hydantoin ring are available some of which contain halogens which are also effective in killing harmful organisms an advantage of the use of DMH is that it limits the types of water purification agents in the water and hence the potential problems that may be caused by the presence of additional complexes in the body of water. Thus the use of a compound containing a hydantoin ring, which has no biocidal effect when used alone, can be used to enhance the purification of the water without introducing water purification agents that of themselves may render the water unsuitable for drinking.

While both a source of silver ions and a compound containing a hydantoin ring can be added in tablet form or the like as illustrated in FIG. 6 a feature of the invention is that the compound containing the hydantoin ring may be added separately and in various quantities dependent on the state of the non-potable water. As the water bottles are transportable to different locations there may be some geographical locations where more purification is required and somewhere less water purification is required. In some instance the source of silver ions, for example silver chloride, which is supported by a carrier, may be used as the sole water purification material. If the person is traveling to a different geographical location where the water is less potable the use of silver chloride or the like as the water purification material in the non-potable water may be inadequate because of the natural limits of the solubility of silver. To increase the effectiveness of the water purification material one can add a quantity of a compound containing a hydantoin ring. For example, a tablet containing a hydantoin ring such as DMH can be added to the container to increase the solubility of silver in the water in the container and hence the effectiveness of the water purification material. The tablets may can be sized to increase the solubility of silver to predetermined levels and hence the effectiveness of the water purification material to different levels.

A further feature of the invention is that in household applications in different geographical regions one may use the same water purification agent i.e. a source of silver ions such as silver chloride however the amount of compounds containing a hydantoin ring i.e. DMH may be adjusted to levels to bring the silver solubility up to levels where the silver alone is effective in purifying the non-potable water. Consequently, the level of effectiveness of the water purification material can be enhanced to the desired level by the addition of a compound containing a hydantoin ring even though the compound containing a hydantoin ring lacks any biocidal properties.

FIGS. 7 shows still another example of a water purification device for use in household where one may want more than a container of water. For example where many members of a family or a community require a source of purified drinking water. In this embodiment the water container 61 is supported by a set of four legs 62. Located at the bottom of container 61 is a source of silver ions and a compound containing a hydantoin ring 64, for example DMH, to generate silver ions to kill the harmful organism in the non-potable water. Attached to the bottom of container 61 is an extension 69 which is shown partially in section to reveal a filter media therein. A valve housing 65 includes a valve handle 67 that can be opened to allow water to flow through spigot 66. Typicality in this embodiment a few gallons of water can be purified.

As FIG. 7 shows one may have household water purification system for insitu generation of potable water comprising a container having an opening in the container for introducing water to be purified. The water purification material which may comprise a source of silver ions and a compound containing a hydantoin ring where the compound containing the hydantoin ring is used to elevate the solubility of the silver ions in the water to be purified to a level above the normal water solubility of silver ions in the non-potable water. The outlet for the potable water may a faucet or spigot as shown in FIG. 7 or the outlet and the inlet may be the same in which case the water can be drawn or scooped out of container 61 on an as needed basis.

A further benefit of the invention described herein is that one can adjust the silver solubility in water to respond to the water conditions. That is, if the non-potable water contains relatively few harmful organisms little or no DMH may be used. On the other hand if the water contains substantially amount of harmful organisms, which can not be effectively controlled with the use of the metal ions alone, one can add DMH or any other compound containing a hydantoin ring until the solubility of silver in the water increases to a level where the silver ions can quickly and effectively bring the non-potable water to a potable state.

Thus a feature of the invention is a novel method of purifying water in a container by introducing a non-potable water, a source of silver ions and a compound containing a hydantoin ring into the container to increase the natural water solubility of silver ions; and converting the non-potable water into potable water by exposing the non-potable water to the source of silver ions and the compound containing a hydantoin ring. The method of purifying water may include introducing sufficient compound containing a hydantoin ring such as DMH into the nonpotable water to increase the solubility of silver ions to a level sufficient to purify the non-potable water. For example, in the particular geographical area one may increase the level of silver solubility in excess of 50 ppb. If desired, once the non potable water becomes potable one has the option of removing silver ions from the potable water with an ion exchange resin to reduce the silver ions to a desired level.

Figure 8:
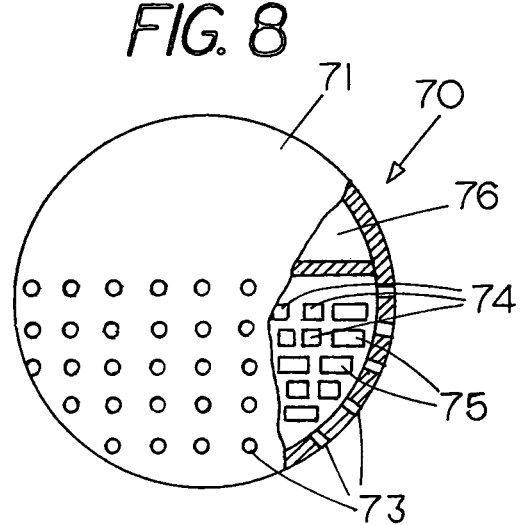
FIG. 8 is a partial sectional view of a dispenser holding a water purification material.

FIG. 8 shows an example of a dispenser 70 for use with non-potable water that may be held in a container for daily drinking therefrom by one or more persons. Typically, such containers may hold as little as a gallon of non-potable water or they may contain many gallons of non-potable water. Dispenser 70 is well suited for purification of small amounts of non-potable water found in open water lakes although it may be used with other sources of non-potable water. Lake water which is used for human consumption may be found in various geographic regions but oftentimes is prevalent in wilderness areas, particularly in areas where there are lake cabins and no wells for drawing water. In these areas a bucket or pail of non-potable water may be retrieved from the lake and carried to a cabin where the non-potable water is purified for drinking. To purify a container of non-potable water dispenser 70 is merely placed in the pail of non-potable water.

FIG. 8 shows the dispenser 70 comprise a spherical housing 71 with a plurality of openings 73 therein for ingress and egress of water. Housing 71 is typically made from a polymer plastic or the like to form an enclosure for the water purification material. In this example the water purification material comprises a source of silver ions 74 and a compound containing a hydantoin ring 75. The combination increases the solubility of the silver ions in the non-potable water to quickly convert the non-potable water in the container into potable water without the aid of additional water purification agents. With this particular dispenser one need only draw a pail of water and place the dispenser with the water purification material in the pail of non-potable water. The dispenser and the water purification may be sized for use with only a single pail of water or it may be sized for extended use. If the dispenser is sized for multiple uses the person would remove the dispenser from the pail when empty, again fill the pail with non-potable water and then place the dispenser 70 in the pail of non-potable water to convert the non-potable water into potable water. This type of in-situ purification is well suited for containers of five gallons or less since such containers can be readily carried by one person as he or she retrieves a container of non-potable water. Although well suited for small containers if desired the dispenser may be used with larger containers for example in containers which may hold up to 2000 gallons of water. In such cases two or more dispensers may be used to purify the non-potable water in the container.

In the example shown the dispenser 70 includes a floatation chamber 76 which allows the dispenser 70 to float while the submerged portion of the dispenser containing the water purification material 74, 75 is in contact with the non-potable water through the ingress and egress of water through apertures 73.

This type of dispenser is also well suited for placement in community containers such as container 60 which is shown in FIG. 7. An advantage of the floating dispenser is that one can quickly tell of the non-potable water has been converted to potable water by the mere presence of the floating dispenser. It should be pointed out that although a hollow spherical housing 70 is shown other shapes for the dispenser housing may be used without departing from the spirit and scope of the invention.

Figure 9:
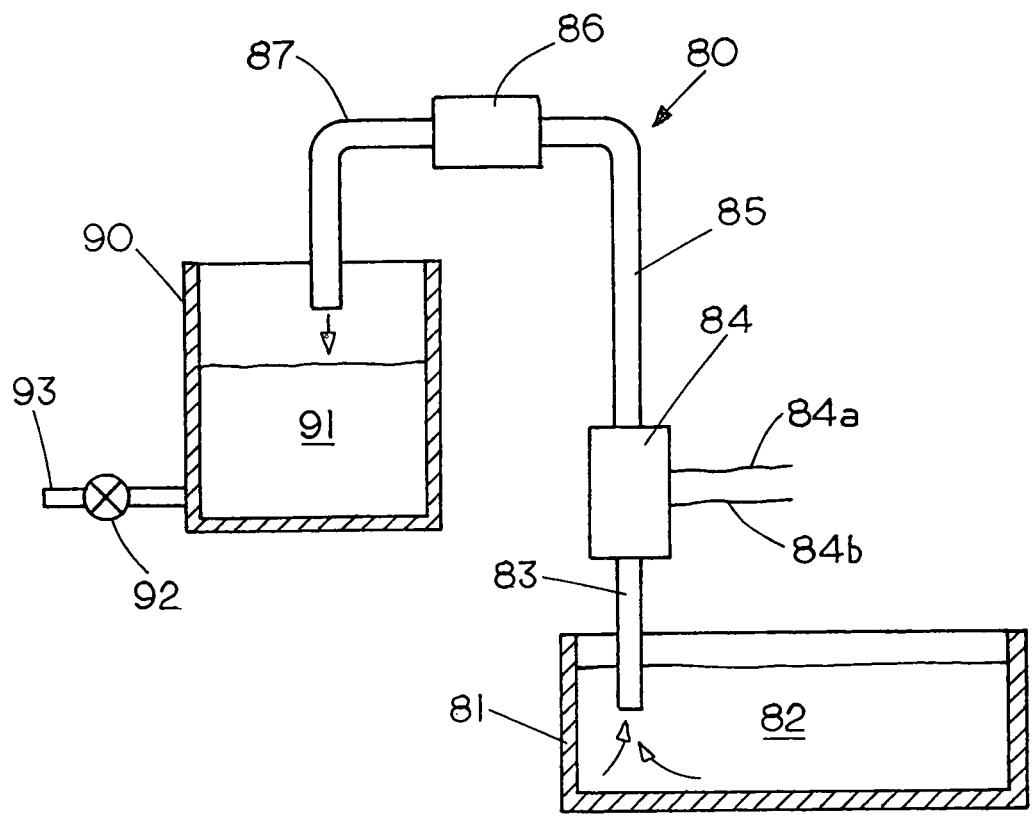
FIG. 9 shows a water purification that converts non-potable water to potable water by pumping the non-potable water through the water purification material.

FIG. 9 shows a water purification system 80 that converts non-potable water to potable water by pumping non-potable water through the water purification material. System 80 includes a container 81 with non-potable water 82 located therein. One end of a pipe 83 extends into the non-potable water 82 and the other end into a water inlet in an electric pump 84 with pump 84 having electrical leads 84*a* and 84*b* for receiving power to operate pump 84. The water pump outlet 85 connects to a housing 86 which contains the water purification material as described hereinabove. As the non-potable water is pumped through housing 86 the water is purified. That is the water purification material comprising a source of silver and a compound containing a hydantoin ring converts the non-potable water into potable water. The potable water then flows from housing 86 through pipe 87 which directs the potable water 91 into container 90. The potable water 91 can then be drawn as needed from the container 90 through a valve 92 and spout 93.

It is envisioned that the electric water pump 84 may be powered by solar power or other sources of available power. If desired, a mechanical pump may be used to draw the non-potable water from the container 81. While larger quantities of non-potable water can be converted into potable water a feature of the invention herein that allows one to quickly convert small quantities of non-potable water into potable water on-the-go. For example container 90 may be a drinking glass or other type of drinking container to allow a person to drink the potable water once it has been discharged from pipe 87.

I claim:

1. A portable hand held water purification device comprising:
   a container suitable for grasping in a user's hand with said container including a water chamber therein;
   an opening in the container for introducing non-potable water to be purified into the water chamber;
   a drinking tube having a first end located within said container and a second end extending out of said container;
   a housing containing a porous structure located proximal said first end of said drinking tube;
   a water purification material located within said housing on the porous structure, said water purification material retained in a water contacting condition in said water chamber, said water purification material comprises a source of silver ions and a compound containing a hydantoin ring whereby the solubility of the silver ions in the non-potable water is increased by the presence of the compound containing the hydantoin ring therein to thereby enhance the ability of the water purification material to quickly convert the non-potable water into potable water without the aid of additional water purification agents; and
   a filter media located between said water purification material and said second end of said drinking tube, said filter media lowering the level of silver ions in said water before ingestion by the user through said drinking tube.

2. The portable hand held water purification device of claim 1 wherein the non-potable water includes halides that limit the solubility of silver in the non-potable water to a level of silver solubility which is insufficient to convert the non-potable water to potable water in the absence of the compound containing a hydantoin ring.

3. The portable hand held water purification device of claim 2 wherein the filter media is an ion exchange medium to reduce the level of silver ions in the potable water to less than 50 ppb.

4. The portable hand held water purification device of claim 3 wherein the compound containing the hydantoin ring is either glycolylurea or Dimethylhydantoin and the compound is maintained in contact with the nonpotable water in the container and the source of silver ions is silver metal.

5. The portable hand held water purification device of claim 4 including a cover for forming a closure to the container so that engagement of the cover brings the water purification material into contact with the non-potable water to be purified.

6. The portable hand held water purification device of claim 3 wherein the compound containing a hydantoin ring is added after the source of silver ions has been introduced into the container to increase the solubility of silver in excess of 50 ppb.

* * * * *